United States Patent [19]

Skeels et al.

[11] Patent Number: 5,659,099
[45] Date of Patent: *Aug. 19, 1997

[54] ACTIVATED ZEOLITE BETA AND ITS USE FOR HYDROCARBON CONVERSION

[75] Inventors: Gary W. Skeels, Bethlehem, N.H.; Edith M. Flanigen, White Plains, N.Y.

[73] Assignee: UOP, Des Plaines, Ill.

[*] Notice: The term of this patent shall not extend beyond the expiration date of Pat. No. 5,258,570.

[21] Appl. No.: 395,251

[22] Filed: Feb. 28, 1995

Related U.S. Application Data

[60] Continuation-in-part of Ser. No. 96,808, Jul. 26, 1993, Pat. No. 5,393,718, which is a division of Ser. No. 767,457, Sep. 30, 1991, Pat. No. 5,258,570, which is a continuation-in-part of Ser. No. 596,157, Oct. 11, 1990, Pat. No. 5,095,169, which is a continuation-in-part of Ser. No. 366,263, Jun. 12, 1989, abandoned, which is a division of Ser. No. 175,332, Mar. 30, 1988, abandoned.

[51] Int. Cl.$^6$ ........................................................ C07C 5/22
[52] U.S. Cl. .......................... 585/481; 585/430; 585/434; 585/477; 585/480; 585/482
[58] Field of Search ............................ 585/430, 434, 585/477, 480, 481, 482

[56] References Cited

U.S. PATENT DOCUMENTS

| Re. 28,341 | 2/1975 | Wadlinger et al. | 206/120 |
|---|---|---|---|
| 3,308,069 | 3/1967 | Wadlinger et al. | 252/455 |
| 4,301,316 | 11/1981 | Young | 585/455 |
| 4,428,819 | 1/1984 | Shu et al. | 585/737 |
| 4,501,926 | 2/1985 | LaPierre et al. | 585/739 |
| 4,518,485 | 5/1985 | LaPierre et al. | 208/89 |
| 4,554,065 | 11/1985 | Albinson et al. | 208/59 |
| 4,554,145 | 11/1985 | Rubin | 502/77 |
| 4,568,655 | 2/1986 | Oleck et al. | 502/66 |
| 4,612,108 | 9/1986 | Angevine et al. | 208/111 |
| 4,642,226 | 2/1987 | Calvert et al. | 423/328 |
| 4,647,368 | 3/1987 | McGuiness et al. | 208/60 |
| 4,845,063 | 7/1989 | Chu | 502/60 |
| 5,011,805 | 4/1991 | Dessau | 502/66 |
| 5,095,169 | 3/1992 | Skeels et al. | 585/739 |
| 5,258,570 | 11/1993 | Skeels et al. | 585/739 |
| 5,393,718 | 2/1995 | Skeels et al. | 502/66 |

FOREIGN PATENT DOCUMENTS

| 0159846 | 10/1985 | European Pat. Off. | C01B 33/28 |
|---|---|---|---|
| 0164939 | 12/1985 | European Pat. Off. | C01B 33/28 |
| 0164208 | 12/1985 | European Pat. Off. | C01B 33/28 |

Primary Examiner—Glenn A. Caldarola
Assistant Examiner—Elizabeth D. Wood
Attorney, Agent, or Firm—Thomas K. McBride; John F. Spears, Jr.; Richard E. Conser

[57] ABSTRACT

The present invention relates to a zeolite beta catalyst characterized by critical limits of weak and strong acid species and exceptionally high catalytic activity. The catalyst is activated at a temperature effective to substantially reduce the concentration of strong acid species, i.e., hydronium cations, without substantially reducing the concentration of weak acid species, i.e., hydroxoaluminum cations, preferably following a calcining step wherein a synthesized zeolite beta catalyst containing a templating agent is calcined at a temperature in the range of from about 200° to 1000° C. in order to remove a substantial portion of the catalyst templating agent and an ion-exchanging step wherein the calcined catalyst is ion-exchanged with a salt solution containing at least one hydrogen forming cation selected from $NH_4^+$ and quaternary ammonium. Conversion processes utilizing the catalyst of the invention, including isomerization of paraffins and alkylaromatics and disproportionation of aromatics, also are disclosed.

15 Claims, 4 Drawing Sheets

ACTIVATED ZEOLITE BETA AND ITS USE FOR HYDROCARBON CONVERSION

CROSS-REFERENCE TO RELATED APPLICATIONS

The present application is a continuation-in-part of U.S. Ser. No. 08/096,808, filed Jul. 26, 1993, now U.S. Pat. No. 5,393,718, which is a division of U.S. Ser. No. 07/767,457, filed Sep. 30, 1991, now U.S. Pat. No. 5,258,570, which is a continuation-in-part of U.S. Ser. No. 07/596,157, filed Oct. 11, 1990, now U.S. Pat. No. 5,095,169, which is a continuation-in-part of U.S. Ser. No. 07/366,263, filed Jun. 12, 1989, and now abandoned, which is a division of U.S. Ser. No. 071175,332, filed Mar. 30, 1988, and now abandoned, all of which are incorporated herein by reference thereto.

FIELD OF THE INVENTION

This invention relates to a crystalline microporous three-dimensional solid catalyst having the structure and composition of zeolite beta and at least one enhanced catalytic property and to the use of the catalyst in hydrocarbon-conversion processes.

BACKGROUND OF THE INVENTION

A wide variety of hydrocarbon conversion processes encountered in the petroleum refining industry are catalytic in nature, and many of these processes use crystalline aluminosilicate zeolites as catalysts. Illustrative of such processes include, for example, dewaxing, hydrodewaxing, crocking, hydrocracking, alkylation, isomerization, aromatization, disproportionation and the like. Often, the products from such hydrocarbon conversion processes, or portions thereof, are admixed as blending components to form motor fuels such as gasoline.

Crystalline aluminosilicate zeolites have been used in a variety of catalysts for the conversion of hydrocarbons. Both natural and synthetic crystalline aluminosilicates have been employed. Often the zeolites comprise a noble metal such as platinum or palladium. Included among these are the Type X and Type Y zeolites, ZSM-5 and ZSM-20 zeolites, mordenite, as well as zeolite beta.

U.S. Pat. No. 3,308,069 and Re. 28,341, both issued to Wadlinger et al., disclose a method for preparing zeolite beta. The patents disclose that zeolite beta is prepared from reaction mixtures containing tetraethylammonium hydroxide as the alkali and more specifically by heating in aqueous solution a mixture of the oxides or of materials whose chemical compositions can be completely represented as mixtures of the oxides $Na_2O$, $Al_2O_3$, $[(C_2H_5)_4N]_2O$, $SiO_2$ and $H_2O$ suitably at a temperature of about 75°–200° C. until crystallization occurs. The product which crystallizes from the hot reaction mixture is separated, suitably by centrifuging or filtration, washed with water and dried. The material so obtained may be calcined by heating in air or an inert atmosphere at a temperature in the approximate range of 400°–1700° F. or higher so long as the temperature is not sufficient to destroy the crystallinity.

U.S. Pat. No. 4,642,226, issued to Calvert et al., relates to a new and improved form of crystalline silicate having the structure of zeolite beta, to a new and useful improvement in synthesizing said crystalline silicate and to the use of said crystalline silicate as a catalyst for organic compound, e.g., hydrocarbon compound, conversion. The patent discloses the use of dibenzyldimethylammonium as a directing agent, i.e., templating agent, instead of tetraethylammonium hydroxide as described above. The patent further discloses that the zeolite beta can be ion-exchanged by conventional techniques with a salt solution. Following contact with the salt solution of the desired replacing cation, the zeolite is then preferably washed with water and dried at a temperature ranging from 65° to about 315° C. and thereafter may be calcined in air or other inert gas at temperatures ranging from about 200° to about 600° C., preferably from about 200° to about 550° C. for periods of time ranging from 1 to 48 hours or more to produce a catalytically active thermal decomposition product thereof. The patent discloses the use of zeolite beta in hydroisomerization of normal paraffins, when provided with a hydrogenation component, e.g., platinum.

U.S. Pat. No. 4,428,819, issued to Shu et al., discloses a process relating to the hydroisomerization of catalytically dewaxed lubricating oils using zeolite beta. The patent discloses that when the zeolites have been prepared in the presence of organic cations they are catalytically inactive, possibly because the intracrystalline free space is occupied by organic cations from the forming solution. It is further disclosed that the zeolites may be activated by heating in an inert atmosphere at 540° C. for one hour, for example, followed by base exchange with ammonium salts followed by calcination at 540° C. in air.

U.S. Pat. No. 4,554,145, issued to Rubin, discloses a method for the preparation of zeolite beta. In similar fashion to above cited U.S. Pat. No. 4,642,226, the patent discloses that the synthesized zeolite beta can be ion-exchanged with a salt and thereafter calcined in air or other inert gas at temperatures ranging from about 200°–550° C. for periods of time ranging from 1 to 48 hours or more to produce a catalytically active thermal decomposition product thereof. The patent discloses the use of zeolite beta in hydroisomerization of normal paraffins, when provided with a hydrogenation component, e.g., platinum.

U.S. Pat. No. 4,612,108 issued to Angevine et al., describes a hydrocracking process for feedstocks containing high boiling, waxy components using a number of sequential beds of hydrocracking catalyst based on zeolite beta. The proportion of zeolite beta in the catalyst increases in sequence so that the final bed has the highest zeolite concentration. The dewaxing activity of the zeolite beta-containing catalysts is stated to be enhanced by the use of sequential beds in this manner. The pour point of the high boiling fraction is reduced, as well as that of the distillate product, permitting part of the high boiling fraction to be included in the distillate product, thereby increasing the useful distillate yield.

U.S. Pat. No. 4,568,655, issued to Oleck et al. discloses a single catalyst system which is capable of demetalizing, hydrotreating and hydrodewaxing petroleum residue in a single stage process. The catalyst system utilized includes one or more metal oxides or sulfides of Group VIA and Group VIII of the periodic table impregnated on a base of refractory oxide material and zeolite beta. The catalyst also has about 75% of its pore volume in pores no greater than 100 Å units in diameter and about 20% of its pore volume in pores greater than about 300 Å units in diameter.

U.S. Pat. No. 4,301,316 issued to Young, relates to a process for the selective alkylation of substituted or unsubstituted benzene compounds with relatively long chain length alkylation agents to produce phenylalkanes having an improved yield of the more external phenyl isomers. The reaction can be carried out in the presence of a crystalline zeolite catalyst such as zeolite beta.

U.S. Pat. No. 4,501,926, issued to LaPierre et al., discloses that petroleum distillate feedstocks may be effectively dewaxed by isomerizing the waxy paraffins without substantial cracking. The isomerization is carried out over zeolite beta as a catalyst and may be conducted either in the presence or absence of added hydrogen. The catalyst may include a hydrogenation/dehydrogenation component such as platinum or palladium in order to promote the reactions which occur. The hydrogenation/dehydrogenation component may be used in the absence of added hydrogen to promote certain hydrogenation/dehydrogenation reactions which will take place during the isomerization.

U.S. Pat. No. 4,518,485, issued to LaPierre et al., relates to a process for dewaxing a hydrocarbon feedstock with a relatively high pour point and containing paraffins selected from the group of normal paraffins and slightly branched paraffins and sulfur and nitrogen compounds which comprises subjecting said oil to hydrotreating in a hydrotreating zone operated at hydrotreating conditions sufficient to remove at least a portion of said sulfur and nitrogen compounds and subjecting said hydrotreated oil to catalytic dewaxing by contacting said oil with a catalyst comprising zeolite beta having a silica/alumina ratio of at least 30:1 and a hydrogenation component under isomerization conditions.

U.S. Pat. No. 4,554,065, issued to Albinson et al. describes a process for dewaxing a hydrocarbon feedstock with a relatively high pour point and containing paraffins selected from the group of normal paraffins and slightly branched paraffins which comprises subjecting said feedstock to catalytic dewaxing at catalytic dewaxing conditions by passing said feedstock, along with hydrogen, over a dewaxing catalyst comprising zeolite beta having a noble metal hydrogenation/dehydrogenation component to produce a partially dewaxed product and subjecting said partially dewaxed product to catalytic dewaxing at catalytic dewaxing conditions by passing said partially dewaxed product over a catalyst comprising zeolite beta having a base metal hydrogenation/dehydrogenation component to recover a substantially dewaxed product as a product of the process.

European Patent Application No. 0 159 846, European Patent Application No. 0 164 939 and European Patent Application No. 0 164 208 disclose particular preparation methods of zeolite beta and the use of zeolite beta in hydroisomerization of normal paraffins, when provided with a hydrogenation component, e.g., platinum.

U.S. Pat. No. 4,647,368, issued to McGuiness et al., describes an upgrading process for paraffinic naphthas which subjects a full range naphtha to hydrocracking over a zeolite beta hydrocracking catalyst to effect a selective partial hydrocracking in which the higher molecular weight n-paraffinic components of the naphtha are hydrocracked preferentially to the lower molecular weight components with concurrent isomerization of n-paraffins to isoparaffins, to form a hydrocracked effluent which comprises isobutane, $C_5$–$C_7$ paraffins and relatively higher boiling naphthenes and paraffins. The hydrocracked effluent is split to remove the isobutane and the $C_5$ and $C_7$ paraffins with the balance of the higher boiling components being used as a reformer feed. Removal of the $C_5$ and $C_7$ paraffins permits improved reformer operation with the production of a higher octane product. The isomerization of the paraffins which occurs in the hydrocracking step provides a $C_5$–$C_7$ paraffinic fraction which is of relatively higher octane number because of the shift to isoparaffins, permitting this component to be used as a gasoline blending component.

U.S. Pat. No. 4,845,063, issued to Chu, teaches a zeolite containing a metal of Group IB which preferably is silver. The zeolite may be activated by heating in an inert atmosphere at 540° C., ammonium-exchanged followed by calcination at 540° C. in air. After loading with silver the zeolite is calcined at 540° C. to 900° C., preferably at 750° C. to 875° C.

U.S. Pat. No. 5,011,805, issued to Dessau, discloses a non-acidic reforming catalyst containing zeolite beta and a Group VIII metal which preferably is platinum. The zeolite containing the Group VIII metal is subjected to thermal treatment at a temperature between 150° and 500° C.

It can be seen from the disclosures of the above-cited patents that zeolite beta has been prepared for use as a catalyst in various hydrocarbon-conversion processes. However, none of the references disclose zeolite beta having the unique characteristics of the present invention which provide particular utility in hydrocarbon-conversion processes.

SUMMARY OF THE INVENTION

The present invention relates to a crystalline microporous three-dimensional solid catalyst having the structure and composition of zeolite beta whose catalytic activity is enhanced by a method comprising heating the catalyst in air or an inert atmosphere at a temperature effective to result in a very low concentration of strong acid species and a high concentration of weak acid species.

More specifically, a "volcano effect" is obtained on the activity of a crystalline microporous three-dimensional solid catalyst having the structure and composition of zeolite beta, which previously had been subjected to calcination by heating in air or an inert atmosphere at a temperature and for a period of time sufficient to oxidize at least a substantial portion of a catalyst templating agent initially present on the catalyst, by a method comprising the steps of: (1) ion-exchanging the catalyst with a salt solution containing at least one hydrogen-forming cation other than hydronium; and (2) activating the catalyst by heating in air or an inert atmosphere at a critical temperature of from about 600° to 675° C.

In another aspect of the invention there is provided a process for the conversion of hydrocarbons which comprises contacting a hydrocarbon feedstock with an activated zeolite beta catalyst in a reaction zone at hydrocarbon-conversion conditions wherein said zeolite beta catalyst has catalytic activity enhanced by a method comprising heating the catalyst in air or an inert atmosphere at a temperature effective to result in a very low concentration of strong acid species and a high concentration of weak acid species.

DETAILED DESCRIPTION OF THE INVENTION

Figure 1:
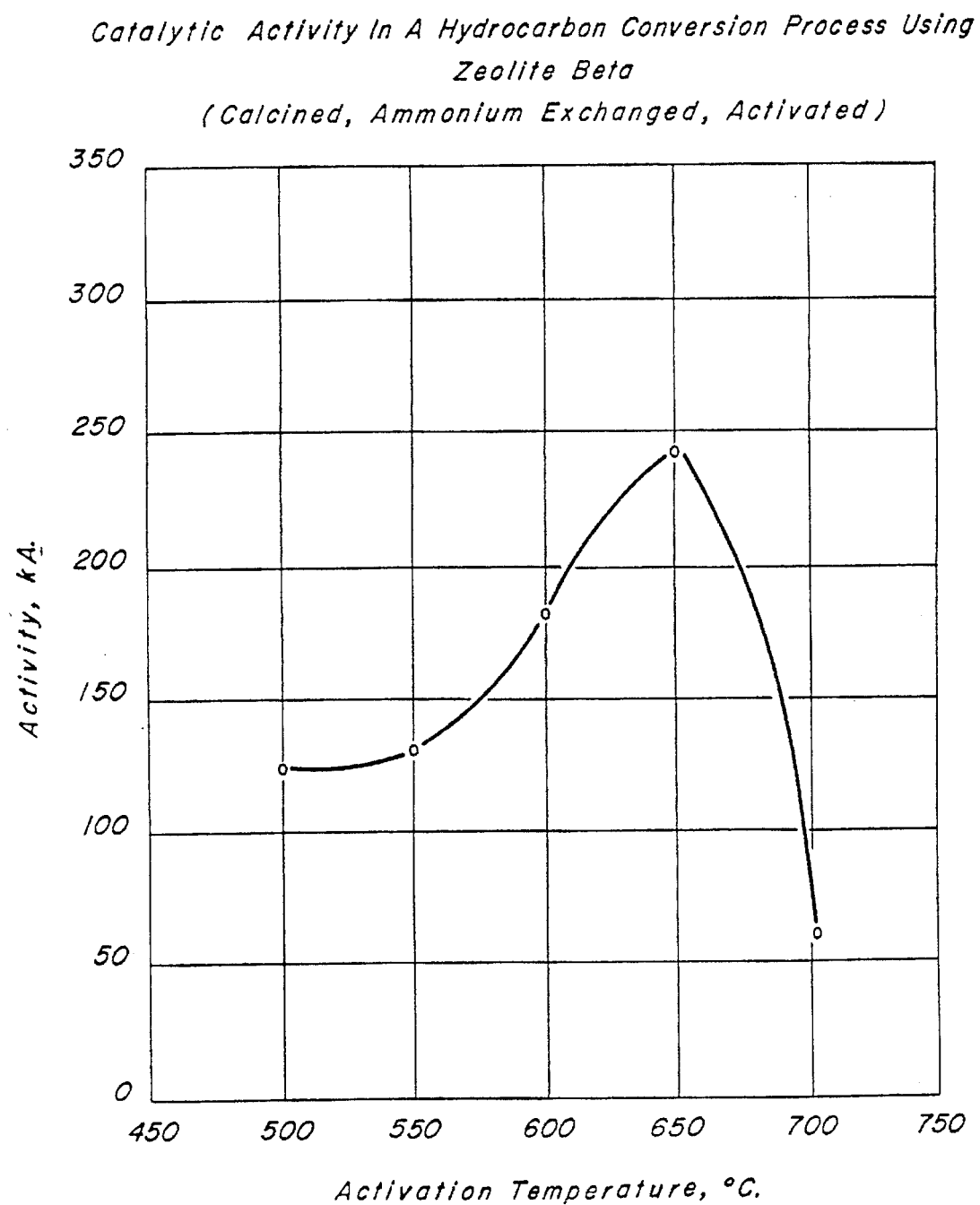
FIG. 1 graphically illustrates the relationship between catalyst cracking activity and catalyst activation temperature in a hydrocarbon conversion process using a zeolite beta catalyst that was calcined at 600° C., ammonium-exchanged and activated.

The crystalline microporous three-dimensional solids having the structure and composition of zeolite beta (hereinafter also denoted as "zeolite beta") employable in the catalyst compositions herein are conventional materials and are described, for example, in above-cited U.S. Pat. No. 3,308,069 and U.S. Reissue Pat. No. 28,341 hereby incorporated by reference. Catalyst compositions for use in the hydrocarbon conversion processes described herein include zeolite beta generally in conjunction with at least one inorganic oxide matrix component as more fully described hereinafter.

The composition of zeolite beta in its as-synthesized form can be represented as follows:

$$[XNa(1.0\ 0.1-X)TEA]\ AlO_2\ YSiO_2$$

where X is less than 1, preferably less than 0.75; TEA represents the tetraethylammonium ion from the templating agent; Y is greater than 5 but less than 100. In the as-synthesized form, water of hydration may also be present in ranging amounts.

The sodium can be derived from the synthesis mixture used to prepare zeolite beta. This synthesis mixture typically contains a mixture of the oxides (or of materials whose chemical compositions can be completely represented as mixtures of the oxides) $Na_2O$, $Al_2O_3$, $[(C_2H_5)_4N]_2O$, $SiO_2$ and $H_2O$. Preferably, the mixture is held at a temperature of about 75°–200° C. until crystallization occurs. The composition of the reaction mixture expressed in terms of mole ratios, preferably falls within the following ranges:

$SiO_2/Al_2O_3$—10 to 200;

$Na_2O$/tetraethylammonium hydroxide (TEAOH)—0.0 to 0.1;
$TEAOH/SiO_2$—0.1 to 1.0; and
$H_2O/TEAOH$—20 to 75.

The product which crystallizes from the hot reaction mixture is separated, suitably by centrifuging or filtration, washed with water and dried.

The material so obtained should then be calcined by heating preferably in air or an inert atmosphere at a temperature usually within the range of from about 200° to about 1000° C. or higher, preferably from about 550° to about 750° C., more preferably from about 575° to about 675° C., and most preferably from about 600° to about 650° C., and for a period of time preferably in excess of 0.25 hours, more preferably in excess of 0.50 hours. The calcination should preferably not cause degradation of any catalytic sites in zeolite beta. This calcination oxidizes and/or decomposes at least a substantial portion of the catalyst templating agent, e.g., tetraethylammonium ions or dibenzyldimethylammonium ions when used instead, or in addition to TEA, from the catalyst templating agent, to hydrogen ions and removes the water to provide a zeolite beta that is substantially freed of templating agent. The calcined zeolite beta is also known as H-form zeolite beta. As used herein, the terms "at least a substantial portion" and "substantially freed" refer to at least 50 wt. %, preferably at least 75 wt. % and most preferably 100 wt. % oxidation and/or decomposition of the catalyst templating agent from the as-synthesized zeolite beta.

With 100 wt. % oxidation and/or decomposition of the catalyst templating agent, the formula of zeolite beta can then be depicted as follows:

$$[XNa(1.0\ 0.1-X)H]\ AlO_2\ YSiO_2$$

where X and Y are as defined above. The degree of hydration is considered to be zero following the calcination.

The H-form zeolite beta is then preferably ion-exchanged with a salt solution containing at least one hydrogen-forming cation other than hydronium, such as $NH_4^+$ or quaternary ammonium, in which sodium is replaced by the hydrogen-forming cation to give zeolite beta of the formula (anhydrous basis with $NH_4^+$ exchange):

$$[XNH_4^+(10.1-X)H]\ AlO_2\ YSiO_2$$

where X and Y are as defined above.

According to this invention, the hydrogen-forming cation-exchanged form of zeolite beta may optionally be subjected to metal cation-exchange to give a material of the formula (anhydrous basis):

$$\frac{X}{n}\ M(1\ 0.1-X)\ H\ AlO_2\ YSiO_2$$

where X and Y are as described above and n is the valence of the metal M which may be any metal.

According to this invention, the hydrogen-forming cation-exchange form of zeolite beta or the metal cation-exchange form of zeolite beta can preferably be combined with at least one inorganic oxide matrix component and thereafter activated by heating in air or an inert atmosphere at a temperature and for a period of time sufficient to enhance at least one catalytic property of the catalyst in a hydrocarbon isomerization process as described hereinafter. The $SiO_2/Al_2O_3$ molar ratio of zeolite beta product employed in this invention will generally be in the range of from about 15:1 to about 45:1, preferably from about 20:1 to about 30:1; and more preferably from about 22:1 to about 26:1.

Because a templating agent such as tetraethylammonium hydroxide is used in its preparation, zeolite beta may contain occluded tetraethylammonium ions, e.g., as the hydroxide or silicate, within its pores in addition to that required by electroneutrality and indicated in the calculated formulae herein. The formulae are calculated using one equivalent of cation per aluminum atom in tetrahedral coordination in the crystal lattice.

Zeolite beta, in addition to possessing a composition as defined above, may also be characterized by its X-ray diffraction data which are set out in U.S. Pat. No. 3,308,069 and U.S. Reissue Pat. No. 28,341. The significant d values (Angstroms, radiation: K alpha doublet of copper, Geiger counter spectrometer) are as shown in Table 1 below:

TABLE 1

| d Values of Reflections in Zeolite Beta |
|---|
| 11.40 + 0.2 |
| 7.40 + 0.2 |
| 6.70 + 0.2 |
| 4.25 + 0.1 |
| 3.97 + 0.1 |
| 3.00 + 0.1 |
| 2.20 + 0.1 |

As indicated above, zeolite beta is preferably ion-exchanged following calcination to remove the organic template by contacting (with or without the presence of an inorganic oxide matrix component) said zeolite beta with a salt solution of at least one hydrogen-forming cation, such as $NH_4^+$ or quaternary ammonium. Zeolite beta may optionally be metal cation-exchanged following the hydrogen-forming cation-exchange. Suitable metal cations include cations selected from the group consisting of cations of Group IIA, Group IIIA, Groups IIIB–VIIB, e.g., nickel, cobalt, iron, manganese, copper, platinum, palladium, rhodium and the like including mixtures thereof, and rare earth cations selected from cerium, lanthanum, praseodymium, neodymium, promethium, samarium, europium, gadolinium, terbium, dysprosium, hoimium, erbium, thulium, ytterbium, lutetium and mixtures thereof. Of course, the metal cation present as a result of metal cation-exchange should have no substantial adverse effect on the desired hydrocarbon conversion process. As a result of such ion-exchange, the zeolite beta can contain at least one cation, e.g., hydrogen-forming cation and/or metal cation, which is different from the cations initially associated with zeolite beta as a result of its synthesis. The cation(s) present as a result of ion-exchange is preferably present in an effective amount between about 0.1 wt. % and about 20 wt. %, based on the weight of the starting zeolite beta and is typically present in an effective amount between about 0.5 wt. % and about 10 wt. %.

The ion-exchange is generally carried out by preparing a slurry of the zeolite beta catalyst by adding about 5 to 15 volumes of water per volume of catalyst, after which a solution of a selected cation is added. The ion-exchange is generally carried out at room temperature and the resulting solution is then heated to above about 50° C. and stirred at this temperature for about 0.5 to 3 hours. This mixture is then filtered and water washed to remove excess anion present as a result of the solution of the cation salt.

The zeolite beta is typically employed with at least one inorganic oxide matrix component, which combination is preferably formed after ion-exchange and prior to activation. While zeolite beta can be employed with one or more of a wide variety of inorganic oxide matrix components as hereinafter described, it is important that the pore structure of zeolite beta remain open and readily accessible to the feedstock in order to provide effective catalytic activity. Illustrative inorganic oxide matrix components which may be employed in formulating catalysts, include: amorphous catalytic inorganic oxides such as catalytically active silica/aluminas, clays, silicas, aluminas, silica-aluminas, silica-zirconias, silica-magnesias, silica-thorias, silica-berylias, silica-alumina-thorias, silica-alumina-zirconias, alumina-magnesias, alumina-borias, alumina-titanias and the like and mixtures thereof. The matrix may be in the form of a sol, hydrogel or gel and is typically an alumina, silica or silica-alumina component such as a conventional silica-alumina catalyst, several types available. The matrix may itself provide a catalytic effect, such as that observed for catalytically active silica/aluminas, or it may be essentially inert. The matrix may act as a "binder" in some instances although in some instances the final catalyst may be spray dried or formed without the need of a binder.

These matrix materials may be prepared as a cogel of silica and alumina or as alumina precipitated on the preformed and preaged hydrogel. Silica may be present as a major matrix component in the solids present in the matrix, e.g., present in an amount between about 5 and about 40 wt. % and preferably between about 10 and about 30 wt. %. The silica may also be employed in the form of a cogel comprising about 75 wt. % silica and about 25 wt. % alumina or comprising about 87 wt. % silica and about 13 wt. % alumina. The inorganic oxide matrix component will typically be present in the final catalyst in an amount between about 0 and 99 wt. %, preferably between about 5 and about 90 wt. %, based on the total catalyst. It is also within the scope of the instant invention to employ other materials with the zeolite beta in the final catalysts, including clays, carbon monoxide oxidation promoters, etc.

Representative of matrix systems employable herein are disclosed in British Patent Specification No. 1,315,553, published May 2, 1973 and U.S. Pat. Nos. 3,446,727 and 4,086,187, hereby incorporated by reference.

As above-mentioned, the catalysts of the present invention may be employed with a matrix component and this may be a silica or alumina component. The alumina component may comprise discrete particles of various aluminas, e.g., pseudoboehmite. The alumina component may be in the form of discrete particles having a total surface area, as measured by the method of Brunauer, Emmett and Teller (BET), greater than about 20 square meters per gram ($M^2$/g), preferably greater than 145 $M^2$/g, for example, from about 145 to about 300 $M^2$/g. The pore volume of the alumina component will typically be greater than 0.35 cc/g. The average particle size of the alumina particles is generally less than 10 microns and preferably less than 3 microns. The alumina may be employed alone as the matrix or composited with the other matrix components.

The alumina component may be any alumina and has preferably been preformed and placed in a physical form such that its surface area and pore structure are stabilized so that when the alumina is added to an impure, inorganic gel containing considerable amount of residual soluble salts, the salts will not alter the surface and pore characteristics measurably nor will they promote chemical attack on the preformed porous alumina which could undergo change. For example, the alumina is typically an alumina which has been formed by suitable chemical reaction, the slurry aged, filtered, dried, washed free of residual salt and then heated to reduce its volatile content to less than about 15 wt. %. The alumina component may be present in the final catalyst in an amount ranging between about 5 and about 95 wt. %, preferably between about 10 and about 30 wt. % based on the total catalyst. Further, an alumina hydrosol or hydrogel or hydrous alumina slurry may be used in the catalyst preparation.

Mixtures of zeolite beta and one or more inorganic oxide matrix components may be formed into a final form for the catalyst by standard catalyst forming techniques including spray drying, pelleting, extrusion and other suitable conventional means. The use of spray drying procedures is the preferred means by which catalysts are prepared and such procedures are well known in the art. When the catalyst is formed as extruded pellets and dried in air, such are typically crushed and sized to a size less than 150 microns.

Catalysts containing zeolite beta may be prepared by any conventional method. One method of preparing such catalysts employing silica-alumina and porous alumina is to react sodium silicate with a solution of aluminum sulfate to form a silica/alumina hydrogel slurry which is then aged to give the desired pore properties, filtered to remove a considerable amount of the extraneous and undesired sodium and sulfate ions and then reslurried in water. The alumina may be prepared by reacting solutions of sodium aluminate and aluminum sulfate under suitable conditions, aging the slurry to give the desired pore properties of the alumina, filtering, drying, reslurry in water to remove sodium and sulfate ions and drying to reduce volatile matter content to less than 15 wt. %. The alumina may then be slurried in water and blended in proper amounts, with a slurry of impure silica-alumina hydrogel. The zeolite beta may then be added to this blend. A sufficient amount of each component is utilized to give the desired final composition. The resulting mixture is then filtered to remove a portion of the remaining extraneous soluble salts therefrom. The filtered mixture is then dried to produce dried solids. The dried solids are subsequently reslurried in water and washed substantially free of the undesired soluble salts. The catalyst is then dried with or without heat to a residual water content of less than about 15 wt. %. The catalyst is employed after activation as described hereinbelow.

For purposes of the present invention, the zeolite beta catalyst must be activated by heating in air or an inert atmosphere at an initial temperature effective to form an initial concentration of weak acid species and strong acid species and continuing said heating at an activation temperature effective to substantially reduce the concentration of strong acid species without substantially reducing the concentration of weak acid species, both the weak acid and strong acid species being present in the catalyst prior to the activation.

Many of the references hereinbefore cited disclose that the zeolite beta catalyst should be activated at a temperature of about 540° C. In accordance with the present invention, it is preferred that the activation temperature be effective to reduce the concentration of strong acid species by at least 50% as compared to the concentration of strong acid species remaining after activating at 540° C. Also, it is preferred in accordance with the present invention that the activation temperature be effective to increase the concentration of weak acid species as compared to the concentration of weak acid species remaining after activating at 540° C. In general, the activation temperatures that correspond to the range wherein the concentration of strong acid sites can be substantially reduced without substantially reducing the concentration of weak acid sites is at least about 600° C. and less than about 700° C. Preferably the activation temperature is from about 600°–675° C., especially 625°–675° C.

Representative of the strong acid species are hydronium cations, i.e., $H_3O^+$ and representative of the weak acid species are hydroxoaluminum cations, i.e., $Al(OH)_{3-x}^{x+}$. It is not critical to the present invention how the concentration of the respective acid species is determined. One suitable procedure is set forth in the following reference; D. W. Breck and G. W. Skeels, *ZEOLITE CHEMISTRY I, THE ROLE OF ALUMINUM IN THE THERMAL TREATMENT OF AMMONIUM EXCHANGED ZEOLITE Y*, Proceedings of the Sixth International Congress on Catalysis, Vol. 2, pp. 645–659, The Chemical Society, London, (1977). This procedure generally involves treating the zeolite sample in a sodium chloride solution and then titrating the sample with sodium hydroxide to obtain two end points, one at a low pH, i.e., the strong acid, and one at a high pH, i.e., the weak acid. A result in terms of milliequivalents of sodium hydroxide per gram of zeolite can then be obtained for each acid species and translated to acid concentration.

The activation temperature is effective to reduce the concentration of hydronium cations after activation to a level corresponding to less than 0.2 milliequivalents of NaOH per gram of zeolite beta, and preferably to below 0.1 meq NaOH/gram. Even more preferably, the activation temperature is effective to substantially eliminate the hydronium cations to below detectable levels by the above infraction procedure. It is further preferred that the concentration of hydroxoaluminum cations after activation is increased to a level of at least 0.8 milliequivalents of NaOH per gram of zeolite beta, and especially to a level of 0.9 meq NaOH/gram or more.

When a zeolite beta catalyst is prepared and activated according to the invention, a rapid increase, or "volcano effect", is observed in catalytic activity. The activity kA according to the butane-cracking test described hereinbelow may be increased to about 170 or higher, often to at least 200, and perhaps to 250 or more.

The activation time period is not narrowly critical and typically is in excess of 0.25 hours, preferably in excess of 0.50 hours, so long as the activation period is not sufficient to destroy the crystallinity of zeolite beta. Activation of zeolite beta catalyst for a period of about 1 hour or longer is a preferred aspect of this invention.

It is important to note that the method of the present invention can be performed on a zeolite beta-containing catalyst in any of its stages of existence beyond the as-synthesized stage. That is, the method of the present invention can be performed on zeolite beta in the as-synthesized form, calcined form or in the ion-exchanged form. Moreover, it is to be further understood that the method of the present invention can be used to treat regenerated catalysts as well, e.g., catalysts that have been subjected to oxidative regeneration for carbon removal.

Hence, in one aspect of the present invention, the calcination step can be included in the method, along with ion-exchange and activation steps described above. Thus, the present invention can be practiced on as-synthesized zeolite beta which contains templating agent by including the calcination step in the process.

In another aspect of the present invention, it is not required that the calcination step be performed. For example, a catalyst supplier may provide zeolite beta that has been previously calcined. In such a case, the method would include the ion-exchange step and the activating step as described above.

In still yet another aspect of the present invention, it is not required to perform the ion-exchange step. This would be appropriate when the zeolite beta has already been ion-exchanged as described above and perhaps dried such as when the catalyst is ready for loading in a reactor vessel.

According to the present invention, in a process for catalytically converting a feedstock into a product, a feedstock is contacted with the activated zeolite beta catalyst in a reaction zone at conditions effective to convert the feedstock into a product.

Substantially any feedstock or combination of feedstocks may be employed in the present invention. Such feedstock, i.e., reactant component or components, may be gaseous, solid or liquid at ambient conditions, i.e., 20° C. and atmospheric pressure. The feedstock may be organic or a combination of inorganic and organic components. The present reaction system is particularly applicable to organic feedstocks, preferably having molecules comprising carbon and hydrogen, and optionally one or more other elements. This other element is preferably selected from the group consisting of oxygen, sulfur, halogen, nitrogen, phosphorus and mixtures thereof, with oxygen being particularly preferred.

The product or products obtained from the feedstock/ activated zeolite beta catalyst contacting will, of course, depend, for example, on the feedstock, catalyst and conditions employed. As with the feedstock, the product or products can be organic or a combination of inorganic and organic components. Preferably, the desired product is organic. However, it should be noted that a necessary, and therefore desired, reaction by-product may be inorganic even when the primary product sought is organic. This is exemplified by the conversion of methanol to light olefins plus water. The organic product or products have molecules which preferably include carbon and hydrogen. The desired product or products preferably have kinetic diameters which allow such product or products to be removed from or escape from the pores of the zeolite beta catalyst composition.

The amount of zeolite beta catalyst in the reaction zone may vary over a wide range depending, for example, on the specific processing application involved.

In addition to the feedstock, a diluent may be used in conjunction with the feedstock if desired and/or beneficial to the overall process. Such diluent may be mixed or combined with the feedstock prior to the feedstock/activated zeolite beta catalyst contacting or it may be introduced into the reaction zone separately from the feedstock. Such diluent preferably acts to moderate the rate, and possibly also the extent, of feedstock chemical conversion and may also act to aid in temperature control. In certain embodiments, the diluent is preferably substantially continuously fed to the reaction zone during the process. Typical of the diluents which may be employed in the instant process are helium, argon, nitrogen, carbon monoxide, carbon dioxide, hydrogen, hydrocarbons and mixtures thereof. The amount of diluent employed, if any, may vary over a wide range depending on the particular application involved. For example, the amount of diluent may be in an amount in the range of about 0.1% or less to about 100 times or more of the moles of feedstock.

The conversion conditions at which the process occurs can vary widely depending, for example, on the specific feedstock and catalyst employed and on the specific product or products desired. The present process is particularly applicable with feedstock/activated zeolite beta catalyst contacting temperatures in excess of about 50° C., more preferably in excess of about 100° C., and with pressures of from about atmospheric to about 2000 psig. The residence time of the feedstock in the reaction zone may be independently selected depending, for example, on the specific feedstock and catalyst employed, and on the specific product or products desired.

Preferably the organic feedstock is a hydrocarbon feedstock and the catalytic-conversion process is a hydrocarbon-conversion process. Substantially any hydrocarbon-conversion process which is capable of being catalyzed by a zeolite beta catalyst composition can be conducted in accordance with this invention. Illustrative of such hydrocarbon conversion processes include, for example, cracking, hydrocracking, alkylation for both the aromatic and isoparaffin types, isomerization including normal-paraffin or xylene isomerization, polymerization, reforming, hydrogenation, dehydrogenation, transalkylation, dealkylation, hydrodecyclization and dehydrocyclization.

Using activated zeolite beta catalyst compositions which contain a hydrogenation promoter such as platinum or palladium, heavy petroleum residual stocks, cyclic stocks and other hydrocrackable charge stocks can be hydrocracked at temperatures in the range of 200°–450° C. using molar ratios of hydrogen to hydrocarbon in the range of between 2 and 80, pressures between atmospheric and 200 bar, and a liquid hourly space velocity (LHSV) of from 0.1 to 20, preferably 1.0 to 10.

The activated zeolite beta catalyst compositions employed in hydrocracking are also suitable for use in reforming processes in which the hydrocarbon feedstocks contact the catalyst at temperatures of from about 350°–600° C. and hydrogen pressures of from 1 to 35 bar. LHSV values in the range of 0.1 to 10 and hydrogen to hydrocarbon molar ratios in the range of 1 to 20, preferably between 4 and 12.

Other isomerization reactions are carried out under conditions similar to those described above for reforming, using somewhat more acidic catalysts. Olefins are preferably isomerized at temperatures of 200°–500° C., while heavy paraffins, naphthenes and alkyl aromatics are isomerized at temperatures of 300°–550° C. Particularly desirable isomerization reactions contemplated herein in addition to the normal paraffin isomerization described above include the conversion of n-heptene and/or n-octene to isoheptenes, and isooctenes, methylcyclopentane to cyclohexane, meta-xylene and/or ortho-xylene to para-xylene, 1-butene to 2-butene and/or isobutene, n-hexene to isohexene, cyclohexene to methylcyclopentene, etc.

Isomerization of a $C_8$-aromatics mixture containing ethylbenzene and xylenes is a particularly preferred use of the activated beta zeolite of the invention. Optimally the aforementioned $C_8$ aromatics comprise a non-equilibrium mixture, i.e., at least one $C_8$-aromatic isomer is present in a concentration that differs substantially from the equilibrium concentration at isomerization conditions. Usually the non-equilibrium mixture is prepared by removal of para- and/or ortho-xylene from a fresh $C_8$ aromatic mixture obtained from aromatics production. A suitable $C_8$-aromatics feed mixture may contain nonaromatic hydrocarbons, e.g., naphthenes and paraffins, in an amount up to 30 mass % of the total feed.

Contacting may be effected using the catalyst in a fixed-bed system, a moving-bed system, a fluidized-bed system, or in a batch-type operation, with a fixed-bed system being preferred considering simpler operation and avoidance of attrition losses. The feedstock and hydrogen-rich gas optimally are preheated to the desired reaction temperature and then passed into an isomerization zone containing a fixed bed of catalyst. The conversion zone may be one or more separate reactors with suitable means therebetween to ensure that the desired isomerization temperature is maintained at the entrance to each zone. The reactants may be contacted with the catalyst bed in either upward-, downward-, or radial-flow fashion, and the reactants may be in the liquid phase, a mixed liquid-vapor phase, or a vapor phase when contacted with the catalyst. Alkylaromatic-isomerization conditions as disclosed hereinabove comprise a temperature of from about 300° to 550° C., pressure of from 1 to 35 bar, and LHSV in the range of 0.1 to 10 $hr^{-1}$. Hydrogen if present is supplied at a molar ratio to the $C_8$-aromatics feedstock of 1 to 20.

The particular scheme used to recover an isomerized alkylaromatic product from the effluent of the reactors of the isomerization zone is not deemed to be critical to the instant invention, and any effective recovery scheme known in the art may be used. Typically, after removal of light-hydrocarbon components by flash separation, the condensed liquid product then is fractionated to remove light and/or heavy byproducts and obtain the isomerized product. The product from isomerization of $C_8$ aromatics usually contains a higher proportion of para-xylene than in the feedstock and is processed to selectively recover the para-xylene isomer, optionally by crystallization. Selective adsorption is preferred using crystalline aluminosilicates according to U.S. Pat. No. 3,201,491. Improvements and alternatives within the preferred adsorption recovery process are described in U.S. Pat. Nos. 3,626,020, 3,696,107, 4,039,599, 4,184,943, 4,381,419 and 4,402,832, incorporated herein by reference thereto. Preferably, non-recovered $C_8$-aromatic isomers are recycled to extinction and thus are converted either to para-xylene or by side-reactions. Ortho-xylene separation, preferably by fractionation, also may be effected on the fresh $C_8$-aromatic feed or isomerized product, or both in combination, prior to para-xylene separation.

At somewhat higher temperatures, i.e., from about 350°–550° C., preferably 450°–500° C. and usually at somewhat lower pressures within the range of about 1 to 5 bar, the same catalyst compositions are used to hydroisomerize feedstocks containing heavier normal paraffins. Preferably, the heavy paraffin feedstock comprises normal paraffins having a carbon number range of $C_7$–$C_{20}$. Contact time between the feedstock and the catalyst is generally relatively short in order to avoid undesirable side reactions such as olefin polymerization and paraffin cracking. LHSV values in the range of 0.1 to 10, preferably 1.0 to 6.0 are suitable.

The crystal structure of the activated zeolite beta catalysts and their availability in a form totally void of alkali metal content favor their use in the conversion of alkylaromatic compounds according to the isomerization process described above or disproportionation as described hereinbelow. Suitable alkylaromatic-conversion conditions encompassing these uses, as disclosed herein, encompass a temperature of from about 200° to 550° C., a pressure of from 1 to 150 bar and a liquid hourly space velocity (LHSV) of from 0.1 to 15 $hr^{-1}$.

Another favored use for the activated zeolite beta of the invention in alkylaromatics conversion is the catalytic disproportionation of toluene, ethylene, trimethyl benzenes, tetramethyl benzenes and the like. Disproportionation of toluene yields primarily $C_8$ aromatics and benzene. Disproportionation of $C_9$ aromatics such as trimethylbenzenes, methylethyl benzenes and propylbenzenes yields a range of lighter and heavier aromatic compounds. Disproportionation of a feedstock comprising both toluene and $C_9$ aromatics favors the formation of $C_8$ aromatics, particularly when lighter and heavier aromatics produced in the disproportionation reaction are recycled. In the disproportionation process, isomerization and transalkylation can also occur. Group VIII noble metal adjuvants alone or in conjunction with Group VIB metals such as tungsten, molybdenum and chromium are preferably included in the catalyst composition in amounts of from about 3 to 15 wt. % of the overall composition. Extraneous hydrogen can, but need not, be present in the reaction zone which is maintained at alkylaromatic-disproportionation conditions comprising a temperature of from about 200°–400° C., pressures in the range of 5 to 150 bar and LHSV values in the range of 0.1 to 15.

Catalytic cracking processes are preferably carried out with activated zeolite beta compositions using feedstocks such as gas oils, heavy naphthas, deasphalted crude oil residua, etc., with gasoline being the principal desired product. Temperature conditions of 450°–600° C., LHSV values of 0.5 to 10 and pressure conditions of from about atmospheric to 4 bar are suitable.

Dehydrocyclization reactions employing paraffinic hydrocarbon feedstocks, preferably normal paraffins having more than 6 carbon atoms, to form benzene, xylenes, toluene and the like are carded out using essentially the same reaction conditions as for catalytic cracking. For these reactions it is preferred to use the activated zeolite beta catalyst in conjunction with a Group VIII non-noble metal cation such as cobalt and nickel.

In catalytic dealkylation wherein it is desired to cleave paraffinic side chains from aromatic nuclei without substantially hydrogenating the ring structure, relatively high temperatures in the range of about 450°–600° C. are employed at moderate hydrogen pressures of about 20 to 70 bar, other conditions being similar to those described above for catalytic hydrocracking. Preferred catalysts are of the same type described above in connection with catalytic dehydrocyclization. Particularly desirable dealkylation reactions contemplated herein include the conversion of methylnaphthalene to naphthalene and toluene and/or xylenes to benzene. For dealkylation as well as alkylation processes, the activated zeolite beta compositions having pores of at least 5 Å are preferred. When employed for dealkylation of alkyl aromatics, the temperature is usually at least 175° C. and ranges up to a temperature at which substantial cracking of the feedstock or conversion products occurs, generally up to about 370° C. The temperature is preferably at least 230° C. and not greater than the critical temperature of the compound undergoing dealkylation. Pressure conditions are applied to retain at least the aromatics feed in the liquid state. For alkylation the temperature can be as low as 120° C. but is preferably at least 175° C. In alkylation of benzene, toluene and xylene, the preferred alkylating agent is selected from olefins such as ethylene and propylene.

In catalytic hydrofining, the primary objective is to promote the selective hydrodecomposition of organic sulfur and/or nitrogen compounds in the feed, without substantially affecting hydrocarbon molecules therein. For this purpose it is preferred to employ the same general conditions described above for catalytic hydrocracking, and catalysts of the same general nature described in connection with dehydrocyclization operations. Feedstocks include gasoline fractions, kerosenes, jet fuel fractions, diesel fractions, light and heavy gas oils, deasphalted crude oil residua and the like, any of which may contain up to about 5 wt. % of sulfur and up to about 3 wt. % of nitrogen.

The hydrocarbon-conversion processes may be carried out in a batch, semi-continuous, or continuous fashion. The processes can be conducted in a single reaction zone or a number of reaction zones arranged in series or in parallel, or they may be conducted intermittently or continuously in an elongated tubular zone or a number of such zones. When multiple reaction zones are employed, it may be advantageous to employ one or more of such zeolite beta catalyst compositions in series to provide for a desired product mixture. Owing to the nature of the hydrocarbon conversion process, it may be desirous to carry out the certain processes by use of the zeolite beta catalyst compositions in a dynamic (e.g., fluidized or moving) bed system or any system of a variety of transport beds rather than in a fixed bed system. Such systems would readily provide for any regeneration (if required) of the zeolite beta catalyst compositions after a given period of time. If regeneration is required, the zeolite beta catalyst compositions can be continuously introduced as a moving bed to a regeneration zone where they can be regenerated, such as for example by removing carbonaceous materials by oxidation in an oxygen-containing atmosphere. In the preferred practice of some hydrocarbon conversion processes, the zeolite beta catalyst compositions will be subject to a regeneration step by burning off carbonaceous deposits accumulated during reactions.

According to a preferred aspect of this invention, a normal/non-normal paraffinic hydrocarbon feedstock is contacted with the activated zeolite beta catalyst in a reaction zone at an isomerization temperature at least 300° C. lower than the activation temperature and effective to convert at least a portion of the normal paraffin hydrocarbons into a non-normal paraffin hydrocarbon product.

The hydrocarbon feedstock to the reactor generally comprises normal paraffins in the $C_5$ to about $C_{15}$ carbon atom range and is preferably composed principally of the various isomeric forms of saturated hydrocarbons having from 5 to 6 carbon atoms. Such feedstocks are normally the result of refinery distillation operations, and thus may contain small amounts of $C_7$ and even higher hydrocarbons, but these are frequently present, if at all, only in trace amounts. Olefinic hydrocarbons are advantageously less than about 4 mol. % in the feedstock. Aromatic and cycloparaffin molecules have a relatively high octane number, but are to a substantial degree cracked and/or converted into molecules of much lower octane number in the isomerization process. Accordingly, the preferred feedstock should not contain more than about 25 mol. % combined aromatic and cycloparaffinic hydrocarbons. Advantageously, the $C_5$ and $C_6$ non-cyclic paraffins comprise at least 75 mol. % of the feedstock, with at least 25 mol. % being normal pentane and/or normal hexane. A feedstock of the following composition is typical:

| Components | Weight-% |
|---|---|
| $C_4$ minus | 4.1 |
| i-$C_5$ | 24.5 |
| n-$C_5$ | 27.8 |
| i-$C_6$ | 27.4 |
| n-$C_6$ | 14.7 |
| $C_7$ plus | 1.5 |

In the foregoing description of the preferred feedstocks suitably treated in accordance with the present process, the expression "the various isomeric forms of pentane and hexane" is intended to denote all the branched chain and cyclic forms of the compounds, as well as the straight chain forms. Also, the prefix notations "iso" and "i" are intended to be generic designations of all branched chain and cyclic forms of the indicated compound.

The conditions at which the normal-paraffin hydrocarbon isomerization process occurs can vary widely. The isomerization reaction can be conducted over a wide range of temperatures, but, in general, in the range from about 90° to about 425° C. Preferably, the isomerization temperature is between about 120°–300° C. and more preferably between about 150°–290° C. Space velocities from about 0.25 to about 5 liquid volumes per hour of isomerizable normal-paraffin hydrocarbons per volume of activated zeolite beta catalyst composition are preferred with reaction zone pressures preferably within the range from about 6.9 bar (100 psi) to about 69 bar (1000 psi). it is particularly desirable to carry out the isomerization reaction in the presence of hydrogen preferably in the range from about 0.5 to about 5 moles of hydrogen per mole of isomerizable hydrocarbon. The function of the hydrogen is primarily to improve catalyst life, apparently by preventing polymerization of intermediate reaction products which would otherwise polymerize and deposit on the activated zeolite beta catalyst composition. It is not necessary to employ pure hydrogen since hydrogen containing gases are suitable. Product separation facilities of the isomerization process, such as catalytic conversion of naphthas, are suitable sources of hydrogen-rich gases. These hydrogen-rich gases typically contain light hydrocarbons, e.g., $C_1$–$C_3$, and may also contain other compounds.

The normal-paraffin hydrocarbon conversion process may be carried out in a batch, semi-continuous, or continuous fashion. The process can be conducted in a single reaction zone or a number of reaction zones arranged in series or in parallel, or it may be conducted intermittently or continuously in an elongated tubular zone or a number of such zones. When multiple reaction zones are employed, it may be advantageous to employ one or more of such zeolite beta catalyst compositions in series to provide for a desired product mixture. Owing to the nature of the normal paraffin hydrocarbon isomerization process, it may be desirous to carry out the certain processes by use of the zeolite beta catalyst compositions in a dynamic (e.g., fluidized or moving) bed system or any system of a variety of transport beds rather than in a fixed bed system. Such systems would readily provide for any regeneration (if required) of the zeolite beta catalyst compositions after a given period of time. If regeneration is required, the zeolite beta catalyst compositions can be continuously introduced as a moving bed to a regeneration zone where they can be regenerated, such as for example by removing carbonaceous materials by oxidation in an oxygen-containing atmosphere. In the preferred practice of some normal paraffinic hydrocarbon isomerization processes, the zeolite beta catalyst compositions will be subject to a regeneration step by burning off carbonaceous deposits accumulated during reactions.

Often, portions of the products from the isomerization process as well as other hydrocarbon conversion processes are admixed in various proportions, as blending components, as well as with other blending components to form motor fuels such as gasoline. The details of such blending operations are well known to those in the refining industry and need not be further disclosed herein.

The following examples are illustrative of this invention.

EXAMPLE 1

5.8 grams (anhydrous weight) of sodium aluminate was added to 55.6 grams of 40% tetraethylammonium hydroxide (TEAOH) in a glass beaker and stirred at room temperature for a period of five minutes. The resulting mixture was heated with stirring to reflux and held for two minutes in order to dissolve the sodium aluminate. The resulting solution was pale yellow and the sodium aluminate was incompletely dissolved. The glass beaker was transferred to a cool stirring hot plate and cooled with stirring to room temperature. As the solution cooled, additional fine solids appeared in the solution which adhered to the bottom and sides of the glass beaker. The white solid was scraped from the sides of the glass beaker with a teflon spatula and stirred. Once the sodium aluminate/TEAOH solution was cooled, 145.4 grams of Ludox LS silica was added gradually. The resulting slurry became very thick and additional hand agitation with the teflon spatula was needed to maintain the mixing of the thickening gel. The gel was mixed on the magnetic stirrer for an additional ten minutes after all the Ludox LS silica had been added. The gel was divided in half and placed in separate teflon liners of about 93 grams and 105 grams respectively. Each teflon liner was placed in a stainless steel reactor and digested in an oven at a temperature of 150° C. After six days, the two reactors were removed from the oven and cooled overnight. The contents were combined and slurried with an additional 200 milliliters of deionized water and filtered. The solid product was washed with deionized water to a pH<10. The product was dried at room temperature and, when examined by X-ray powder diffraction, gave the characteristic X-ray powder pattern of zeolite beta. The yield of zeolite beta product was approximately 50 grams. Analyzed properties of the zeolite beta product were as follows:

| | |
|---|---|
| $Na_2O$, wt. % | 0.47 |
| $(TEA)_2O$, wt. % | 18.27 |
| $(NH_4)_2O$, wt.% | — |
| $Al_2O_3$, wt. % | 6.38 |

17

-continued

| | |
|---|---|
| SiO$_2$, wt. % | 75.27 |
| (TEA)$_2$O/Al$_2$O$_3$ | 1.18 |
| (NH$_4$)$_2$O/Al$_2$O$_3$ | — |
| SiO$_2$/Al$_2$O$_3$ | 20.01 |

The zeolite beta product was then calcined in flowing air at a temperature of 600° C. for a period of 2 hours to decompose the tetra-ethylammonium cation. After cooling, the calcined zeolite beta product was exchanged with NH$_4$NO$_3$ solution (5 grams NH$_4$NO$_3$ per gram of calcined zeolite beta product) at reflux (3 times), washed in distilled water and dried at room temperature. Analyzed properties of the calcined, ammonium-exchanged zeolite beta product were as follows:

| | |
|---|---|
| Na$_2$O, wt. % | <0.03 |
| (TEA)$_2$O, wt. % | — |
| (NH$_4$)$_2$O, wt. % | 2.69 |
| Al$_2$O$_3$, wt. % | 6.56 |
| SiO$_2$, wt. % | 89.46 |
| (TEA)$_2$O/Al$_2$O$_3$ | — |
| (NH$_4$)$_2$O/Al$_2$O$_3$ | 0.81 |
| SiO$_2$/Al$_2$O$_3$ | 23.15 |

EXAMPLES 2–11

The calcined, ammonium-exchanged zeolite beta product prepared in Example 1 was tested for n-butane cracking activity utilizing a cylindrical quartz tube reactor (254 millimeters in length and 10.3 millimeters internal diameter). Normal-butane cracking activity is useful screening test for catalytic activity and is indicative of isomerization activity. Separate samples of the calcined, ammonium-exchanged zeolite beta product were tested for n-butane cracking activity. The reactor was loaded with 20–40 mesh (U.S. standard) particles of the calcined, ammonium-exchanged zeolite beta product in an amount of from 0.5 to 5 grams. The calcined ammonium-exchanged zeolite beta product was then activated in the reactor for a period of 1 hour in a stream of either flowing helium or flowing air at the activation temperature indicated in Table A. below. The reaction feedstock was a helium-n-butane mixture containing 2 mol. % n-butane and, after activation of the zeolite beta product, was passed through the reactor at a rate of 50 cubic centimeters per minute with the reactor temperature maintained at 500° C. Analysis of the feedstock and the reactor effluent was carried out using conventional gas chromatography techniques. The reactor effluent was analyzed after 10 minutes of on-stream operation. From the analytical data, a pseudo-first-order rate constant (kA) was calculated. The results are given in Table A. The value of kA is an indication of the level of catalytic activity.

TABLE A

| Example No. | Activation Temperature (°C.) | % Consumption of n-Butane | % i-Butane in Product | kA |
|---|---|---|---|---|
| 2 | 500 Air | 91.3 | 0.4 | 126 |
| 3 | 500 Helium | 88.4 | 1.1 | 128 |
| 4 | 550 Air | 89.1 | 0.2 | 132 |
| 5 | 550 Helium | — | — | — |
| 6 | 600 Air | 93.1 | 0.1 | 184 |
| 7 | 600 Helium | 93.3 | 0.1 | 170 |
| 8 | 650 Air | 98.6 | 0.0 | 245 |
| 9 | 650 Helium | 99.7 | 0.0 | 305 |

18

TABLE A-continued

| Example No. | Activation Temperature (°C.) | % Consumption of n-Butane | % i-Butane in Product | kA |
|---|---|---|---|---|
| 10 | 700 Air | 82.2 | 0.0 | 60 |
| 11 | 700 Helium | — | — | — |

The above results are plotted in FIG. 1. The activity was enhanced substantially at activation temperatures according to the invention, relative to higher and lower temperatures, such that a "volcano effect" of activity relative to temperature was observed.

EXAMPLES 12–17

In order to demonstrate improved catalytic results from high temperature activation of zeolite beta in accordance with the invention, a series of n-butane cracking tests were conducted with LZ-202 for comparison purposes. LZ-202, an omega type zeolite synthesized in an organic free system, is a known active catalyst for hydrocarbon conversion reactions. LZ-202 is available from UOP, Des Plaines, Ill. Separate samples of ammonium-exchanged LZ-202 product were tested for n-butane cracking activity in accordance with the procedure described in Examples 2–11 above. The results are given in Table B below and show no unusual effect in regard to activity. Typically, a temperature of 550° C. in air is observed with most catalytic materials to be the optimum activation temperature for catalysis.

TABLE B

| Example No. | Activation Temperature (°C.) | % Consumption of n-Butane | % i-Butane in Product | kA |
|---|---|---|---|---|
| 12 | 500 Air | 76.8 | 4.1 | 71 |
| 13 | 500 Helium | 82.1 | 3.5 | 57 |
| 14 | 550 Air | 85.5 | 3.1 | 100 |
| 15 | 550 Helium | 74.1 | 4.0 | 60 |
| 16 | 600 Air | 62.5 | 4.6 | 56 |
| 17 | 600 Helium | 56.0 | 5.0 | 37 |

EXAMPLE 18

51.74 grams (anhydrous weight) of sodium aluminate were added to 361.4 grams of 40% tetraethylammonium hydroxide (TEAOH) and mixed on a magnetic stirrer for a period of five minutes at room temperature before heating to reflux. The sodium aluminate did not completely dissolve. The resulting slurry was transferred to a plastic beaker and stirred with a Heidolph mixer fitted with a jiffy pain mix stirrer until it cooled. As the slurry cooled, additional precipitate formed. When cool, 945.1 grams of Ludox LS silica were gradually added with stirring to the sodium aluminate/TEAOH slurry. A very thick gel formed and additional hand agitation was needed to keep the slurry mixing. After all the Ludox LS silica had been added, the gel was mixed for a period of five minutes and it thinned slightly. 1295.5 grams of the gel were transferred to a two liter reactor and digested for a period of seven days at a temperature of 155° C. The reactor was then cooled overnight. Initial filtration was slow, but as the product was washed with deionized water, filtration became easier. After washing until the pH of the filtrate was less than 10, the solid product was dried at room temperature and fully characterized. This preparation had a yield of 350 grams. It had the characteristic X-ray powder pattern of zeolite beta. Analyzed properties of the zeolite beta product were as follows:

| | |
|---|---|
| Na₂O, wt. % | 0.85 |
| (TEA)₂O, wt. % | 15.63 |
| (NH₄)₂O, wt. % | — |
| Al₂O₃, wt. % | 6.12 |
| SiO₂, wt. % | 77.40 |
| (TEA)₂O/Al₂O₃ | 0.94 |
| (NH₄)₂O/Al₂O₃ | — |
| SiO₂/Al₂O₃ | 21.44 |

The zeolite beta product was then calcined in flowing air at a temperature of 600° C. for a period of 2 hours to decompose the tetra-ethylammonium cation. After cooling, the calcined zeolite beta product was exchanged with $NH_4NO_3$ solution (5 grams $NH_4NO_3$ per gram of calcined zeolite beta product) at reflux (3 times), washed in distilled water and dried at room temperature. Analyzed properties of the calcined, ammonium-exchanged zeolite beta product were as follows:

| | |
|---|---|
| Na₂O, wt. % | <0.03 |
| (TEA)₂O, wt. % | — |
| (NH₄)₂O, wt. % | 2.78 |
| Al₂O₃, wt. % | 6.03 |
| SiO₂, wt. % | 90.26 |
| (TEA)₂O/Al₂O₃ | — |
| (NH₄)₂O/Al₂O₃ | 0.90 |
| SiO₂/Al₂O₃ | 25.39 |

EXAMPLES 19–28

Separate samples of the calcined, ammonium-exchanged zeolite beta product prepared in Example 18 were tested for n-butane cracking activity in accordance with the procedure described in Examples 2–11 above. The results are given in Table C below.

TABLE C

| Example No. | Activation Temperature (°C.) | % Consumption of n-Butane | % i-Butane in Product | kA |
|---|---|---|---|---|
| 19 | 500 Air | 87.6 | 1.7 | 139 |
| 20 | 500 Helium | 85.5 | 1.0 | 120 |
| 21 | 550 Air | 85.2 | 0.5 | 123 |
| 22 | 550 Helium | — | — | — |
| 23 | 600 Air | 95.0 | 0.0 | 182 |
| 24 | 600 Helium | 95.4 | 0.1 | 173 |
| 25 | 650 Air | 98.1 | 0.0 | 210 |
| 26 | 650 Helium | 97.6 | 0.0 | 230 |
| 27 | 700 Air | 65.1 | 0.4 | 71 |
| 28 | 700 Helium | — | — | — |

In order to demonstrate the unique nature of this invention, the following Examples 29–36 were conducted wherein the required activation step or one or more of the preferred treatment steps were omitted, i.e., calcination, and/or ion-exchange.

EXAMPLES 29–32

A zeolite beta product was prepared in accordance with the procedure described in Example 18 above except without the final activating step and without the ammonium exchange step. The zeolite beta product was tested for n-butane cracking activity in accordance with the procedure described in Examples 2–11 above. The results are given in Table D below. The results demonstrate inferior activity of this zeolite beta product in comparison with zeolite beta product prepared according to this invention and further demonstrate the importance of the required catalyst preparation step.

TABLE D

| Example No. | Calcination Temperature (°C.) | % Consumption of n-Butane | % i-Butane in Product | kA |
|---|---|---|---|---|
| 29 | 550 Air | 23.5 | 6.9 | 22 |
| 30 | 600 Air | 44.8 | 2.3 | 63 |
| 31 | 650 Air | 33.9 | 3.6 | 43 |
| 32 | 700 Air | 46.6 | 1.2 | 43 |

EXAMPLE 33

A zeolite beta product was prepared in accordance with the procedure described in Example 18 above except without the initial calcination step to oxidize the catalyst templating agent. The zeolite beta product was ammonium-exchanged and activated at a temperature of 550° C. in air and thereafter tested for n-butane cracking activity in accordance with the procedure described in Examples 2–11 above. The results are given in Table E below. The results demonstrate inferior activity of this zeolite beta product in comparison with zeolite beta product prepared according to this invention and further demonstrate the importance of the required catalyst preparation steps.

TABLE E

| Example No. | Activation Temperature (°C.) | % Consumption of n-Butazne | % i-Butane in Product | kA |
|---|---|---|---|---|
| 33 | 550 Air | 50.2 | 3.7 | 67 |

EXAMPLE 34

A zeolite beta product was prepared in accordance with the procedure described in Example 18 above except without the ammonium exchange step. Instead, the zeolite beta product was hydronium ion-exchanged after the initial calcination step. The zeolite beta product was tested for n-butane cracking activity in accordance with the procedure described in Examples 2–11 above. The results are given in Table F below. The results demonstrate that hydronium-exchanged zeolite beta results in inferior activity in comparison with ammonium-exchanged zeolite beta.

TABLE F

| Example No. | Activation Temperature (°C.) | % Consumption of n-Butane | % i-Butane in Product | kA |
|---|---|---|---|---|
| 34 | 550 Air | 3.5 | 2.1 | 4 |

EXAMPLES 35–36

A zeolite beta product was prepared in accordance with the procedure described in Example 18 above except the zeolite beta product was hydrothermally treated with steam at a temperature of 600° C. following the ammonium exchange step. The product resulting from the steaming was fully crystalline. The zeolite beta product was then activated at a temperature of 650° C. and thereafter tested for n-butane cracking activity in accordance with the procedure described in Examples 2–11 above. The results are given in Table G below. The results demonstrate that hydrothermal steam calcination or activation of zeolite beta product results in inferior activity in comparison with thermal calcination or activation by heating in air or an inert atmosphere.

TABLE G

| Example No. | Activation Temperature (°C.) | % Consumption of n-Butane | % i-Butane in Product | kA |
|---|---|---|---|---|
| 35 | 650 Helium | 2.8 | 21.1 | 2 |
| 36 | 650 Helium | 5.1 | 18.8 | 3 |

EXAMPLE 37

100 grams of calcined, ammonium-exchanged zeolite beta product prepared as in Example 18 were slurried in a beaker in one liter of distilled water. A second solution containing 0.60 grams of $Pt(NH_3)_4Cl_2$ dissolved in 500 milliliters of distilled water was then added to the zeolite slurry and the zeolite beta was platinum-exchanged. The resulting slurry was then filtered and washed with distilled water, dried, extruded with peptized alumina binder and dried again for a period of sixteen hours. The extrudates contained 0.32 wt. % platinum. The extrudates were split into two batches, one batch was calcined in air at a maximum temperature of 650° C. (hereinafter Catalyst A) and the second batch was calcined in air at a maximum temperature of 540° C. (hereinafter Catalyst B).

EXAMPLE 38

Separate samples of Catalyst A and Catalyst B prepared in Example 37 above were evaluated for $C_5/C_6$ isomerization activity using a fixed bed microreactor unit comprising a stainless steel tube (⅝-inch internal diameter). About 8.0 to 12.0 grams of selected Catalyst A or Catalyst B (40×60 mesh, U.S. Standard) were loaded in the microreactor and reduced under a flow of hydrogen gas at a temperature of greater than 200° C. for a period of sixteen hours. A feed consisting of 60 wt. % n-$C_5$, 35 wt. % n-$C_6$ and 5 wt. % cyclohexane was then introduced into the microreactor at a reaction pressure of 250 psig, a weight hourly space velocity (WHSV) of 1.6 hr.$^{-1}$, a hydrogen/hydrocarbon feed molar ratio of 2 and a reaction temperature specified in Table H below. Products were collected at selected run times and the products were analyzed by gas chromatography. The products were evaluated in several respects by determining:

$$\text{i-}C_5 \text{ Conversion} = \frac{\text{i-}C_5}{\text{i-}C_5 + \text{n-}C_5}$$

$$\text{2,2-DMB (Dimethylbutane) Conversion} = \frac{\text{2,2-DMB}}{\text{Total } C_6 \text{ Paraffins}}$$

as a means to determine the relative extent of conversion of pentane and hexane to isomeric products. The results are set forth in Table H below.

TABLE H

| Catalyst | Reaction Temperature (°C.) | i-$C_5$ Conversion | 2,2-DMB Conversion | $C_5^+$ Yield |
|---|---|---|---|---|
| A | 251.7 | 62.9 | 18.1 | 98.5 |
| A | 260.0 | 68.1 | 19.0 | 97.3 |
| A | 265.6 | 69.2 | 19.2 | 95.7 |
| A | 273.9 | 69.1 | 19.0 | 92.4 |
| B | 251.7 | 55.7 | 13.5 | 98.9 |
| B | 260.0 | 63.1 | 15.1 | 97.8 |
| B | 265.6 | 66.5 | 16.1 | 96.5 |
| B | 273.9 | 68.9 | 18.0 | 93.7 |

Figure 2:
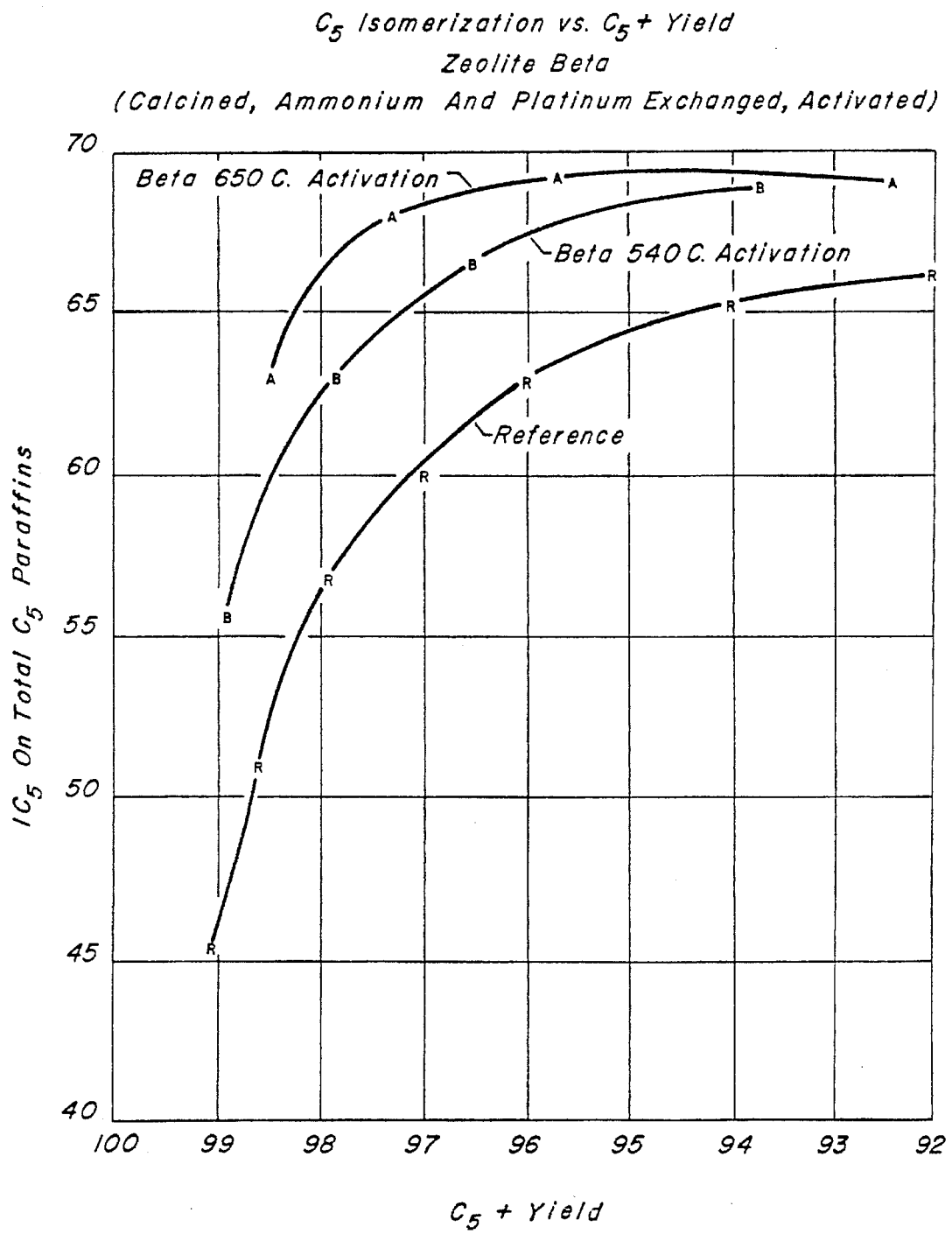
FIG. 2 illustrates the relationship between isomerization and yield of pentanes in a hydrocarbon conversion process using a zeolite beta catalyst that was calcined, ammonium-exchanged, platinum-exchanged and activated.
Figure 3:
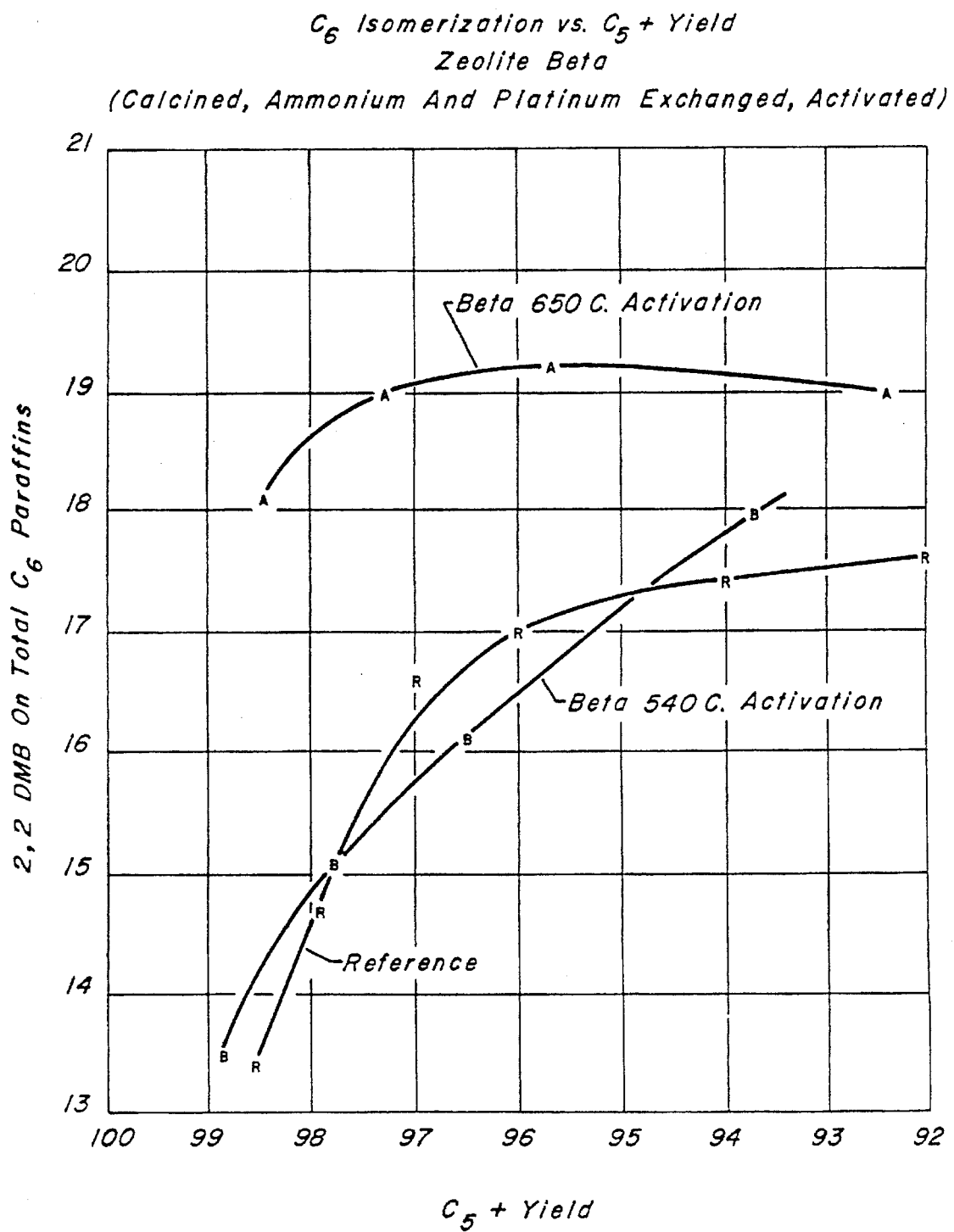
FIG. 3 illustrates the relationship between isomerization and yield of hexanes in a hydrocarbon conversion process using a zeolite beta catalyst that was calcined, ammonium-exchanged, platinum-exchanged and activated.

The results set forth in Table H above are graphically illustrated in FIG. 2 and FIG. 3.

FIG. 2 graphically illustrates the relationship between $C_5$ isomerization conversion and $C_5^+$ yield as demonstrated by the isomerization process described in Example 39, in particular, the relationship between wt. % i-$C_5$ of total $C_5$ paraffins and the wt. % $C_5^+$ yield, utilizing a zeolite beta catalyst activated at a temperature of 650° C., a zeolite beta catalyst activated at a temperature of 540° C. and a standard reference catalyst as identified in Example 39.

FIG. 3 graphically illustrates the relationship between $C_6$ isomerization conversion and $C_5^+$ yield as demonstrated by the isomerization process described in Example 39, in particular, the relationship between wt. % 2,2-DMB (dimethylbutane) of total $C_6$ paraffins and the wt. % $C_5^+$ yield, utilizing a zeolite beta catalyst activated at a temperature of 650° C., a zeolite beta catalyst activated at a temperature of 540° C. and a standard reference catalyst as identified below.

It can be seen from FIGS. 2 and 3 that both the catalytic activity, i.e., conversion, and selectivity, i.e., yield, were substantially enhanced when the catalyst was activated at 650° C. as compared to 540° C. The delta i-$C_5$ conversion, delta 2,2-DMB conversion and delta RON (Research Octane Number) based on a standard reference catalyst were calculated at 96% $C_5^+$ yield using a 60:40 wt. % n-$C_5$: n-$C_6$ feed composition as follows:

delta i-$C_5$ Conversion=i-$C_5$ conversion–63.00 delta 2,2-DMB Conversion=2,2-DMB conversion–17.00 delta RON=0.60×0.33 (i-$C_5$ conversion–63.00)+0.40× 0.65 (2,2-DMB conversion–17.00)

The standard reference catalyst was HS-10, a platinum on H-mordenite catalyst available from Shell Oil Company, The Hague, Netherlands, having an i-$C_5$ conversion of 63% and a 2,2-DMB conversion of 17%. In the formula; 0.60 and 0.40 denote the n-pentane and n-hexane composition of the feed in weight fraction, 0.33 denotes the RON octane difference between isopentane (RON=94) and normal pentane (RON=71) divided by 100, and 0.65 denotes the octane difference between 22DMB (RON=94) and n-hexane (RON=29) divided by 100. The results are set forth in Table I below as follows:

TABLE I

| Catalyst | delta i-$C_5$ Conversion | delta 2-2-DMB Conversion | Delta RON |
|---|---|---|---|
| A | 6.25 | 2.25 | 1.82 |
| B | 4.40 | –0.39 | 0.80 |
| HS-10 | 0.0 | 0.0 | 0.0 |

The results from Table I show superior catalytic performance of zeolite beta activated at a temperature of 650° C. in a $C_5/C_6$ isomerization process in comparison with the catalytic performance of the same catalyst activated at a temperature of 540° C., the typical activation temperature.

EXAMPLE 39

Approximately 1 gram samples on a dry weight basis of the ammonium ion-exchanged zeolite beta, as prepared in Example 1, were activated in a shallow bed under flowing dry air for 2 hours, removed from the oven and placed in a desiccator to cool, then placed in a 50 ml solution of 3.5 M NaCl solution. Potentiometric titrations were then developed with 0.1 N NaOH solution. The result of the titrations shows the amount and type of acidity developed by the zeolite under the various activation conditions.

Figure 4:
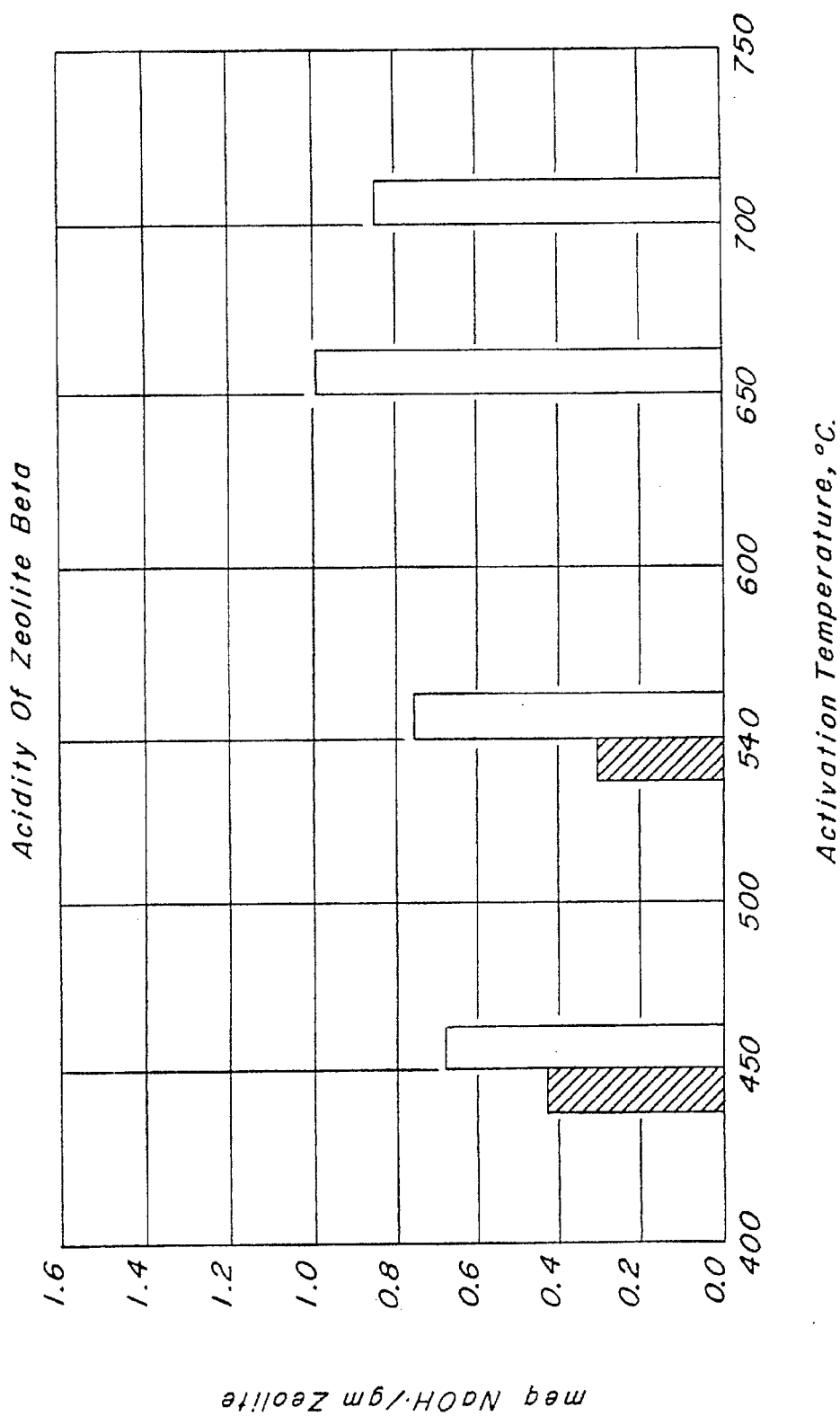
FIG. 4 illustrates the relationship between weak acid species, strong acid species and activation temperature for zeolite beta.

Four samples were activated at 450, 540, 650° and 700° C. and the potentiometric titrations for each sample were developed as described above. The results are plotted in FIG. 4. After 450° C. calcination, two types of acidity were determined, strong acidity from a hydrated proton, $H_3O^+$ and a weaker acid species of hydroxoaluminum cations, $Al(OH)^{2+}$. As the activation temperature was increased, the amount of strong acid decreased as the amount of the weaker acid species increased. Without being bound by any definitive theory, it can be observed that the decrease in strong acidity is accompanied by an increase in weak acidity which corresponds well with the observed isomerization activity shown in Example 38 and FIGS. 2 and 3, and also the n-butane cracking activity shown in Examples 2–11. As the strong acidity ($H_3O^+$), decreases and the weak acidity increases ($Al(OH)^{2+}$), the isomerization activity increases. Enhanced isomerization activity occurs when the strong acidity is no longer observed in the titration and when the weak acidity is also at a maximum. As the weak acidity decreases with calcination above 650° C., the isomerization activity will also be expected to decrease based on the kA values for n-butane cracking, per Examples 2–11.

Although the invention has been illustrated by the preceding examples, it is not to be construed as being limited thereby; but rather, the invention encompasses the generic area as hereinbefore disclosed. Various modifications and embodiments can be made without departing from the spirit and scope thereof. Accordingly, the Examples demonstrate various ways in which the method of the present invention can provide a zeolite beta-containing catalyst that can have at least one enhanced catalytic property, e.g., reactivity, activity or selectivity, for use in hydrocarbon isomerization processes.

We claim:

1. A process for the conversion of alkylaromatic compounds comprising contacting the compounds at alkylaromatic-conversion conditions comprising a temperature of from about 200° to 500° C., a pressure of from 1 to 150 bar and LHSV of from 0.1 to 15 $hr^{-1}$ with an activated zeolite beta catalyst having a concentration of hydroxoaluminum cations corresponding to at least 0.9 milliequivalents of NaOH per gram of zeolite beta and a concentration of hydronium cations corresponding to less than 0.1 milliequivalents of NaOH per gram of zeolite beta to obtain an alkylaromatic product.

2. The process of claim 1 wherein the concentration of hydroninum cations in zeolite beta is not detectable.

3. The process of claim 1 wherein the catalyst comprises at least one inorganic oxide matrix component.

4. The process of claim 3 wherein the matrix component is selected from the group consisting of silica, alumina, magnesia and mixtures thereof.

5. The process of claim 4 wherein the matrix component comprises alumina.

6. The process of claim 1 wherein the catalyst comprises one or more metals selected from the Group VIII noble metals.

7. The process of claim 6 wherein the catalyst further comprises one or more Group VIB metals.

8. The process of claim 1 wherein a hydrogen diluent is used in conjunction with the alkylaromatic compounds.

9. The process of claim 1 wherein the conversion comprises isomerization at alkylaromatic-isomerization conditions to obtain an isomerized alkylaromatic product.

10. The process of claim 9 wherein the alkylaromatic compounds comprise a $C_8$-aromatics mixture and the isomerized product contains a higher proportion of para-xylene than in the feedstock.

11. A process for the isomerization of a $C_8$-aromatics feedstock comprising contacting the feedstock at alkyl, aromatic-isomerization conditions with an activated zeolite beta catalyst having a concentration of hydroxoaluminum cations corresponding to at least 0.9 milliequivalents of NaOH per gram of zeolite beta and a concentration of hydronium cations corresponding to less than 0.1 milliequivalents of NaOH per gram of zeolite beta to obtain an isomerized $C_8$-aromatics product containing a greater proportion of para-xylene than in the feedstock.

12. The process of claim 11 wherein the alkylaromatic-isomerization conditions comprise a temperature of from about 300° C. to 550° C., pressure of from 1 to 35 bar, and LHSV in the range of 0.1 to 10 $hr^{-1}$.

13. The process of claim 12 wherein hydrogen is present in a molar ratio to the $C_8$-aromatics feedstock of 1 to 20.

14. The process of claim 11 wherein the feedstock comprises a non-equilibrium mixture of $C_8$ aromatics.

15. The process of claim 11 further comprising recovery of para-xylene from the isomerized $C_8$-aromatics product.

* * * * *